United States Patent [19]

Jones

[11] Patent Number: 5,213,964
[45] Date of Patent: May 25, 1993

[54] HIGH-DENSITY LIPOPROTEIN SOLID-BASE PRECIPITATION ASSAY METHOD

[75] Inventor: Ronald M. Jones, Mountain View, Calif.

[73] Assignee: Cholestech Corporation, Hayward, Calif.

[21] Appl. No.: 729,447

[22] Filed: Jul. 12, 1991

Related U.S. Application Data

[63] Continuation-in-part of Ser. No. 554,147, Jul. 16, 1990.

[51] Int. Cl.$^5$ .................. C12Q 1/60; C12Q 1/26; G01N 21/77
[52] U.S. Cl. .................. 435/11; 435/25; 436/169; 436/170
[58] Field of Search .................. 435/11, 25; 436/169, 436/170

[56] References Cited

U.S. PATENT DOCUMENTS

| | | | |
|---|---|---|---|
| 4,144,306 | 3/1979 | Figueras | 422/56 |
| 4,477,575 | 10/1984 | Vogel et al. | |
| 4,544,630 | 10/1985 | Ziegenhorn et al. | 435/11 |
| 4,615,946 | 10/1986 | Temple | 428/361 |
| 4,826,761 | 5/1989 | Aria et al. | 435/11 |
| 4,987,085 | 1/1991 | Allen et al. | 436/169 |
| 5,082,626 | 1/1992 | Grage | 436/165 |

FOREIGN PATENT DOCUMENTS 1211707 9/1986 Canada.
0415298 3/1991 European Pat. Off. .............. 435/11

OTHER PUBLICATIONS

Bachorik, P. S., Methods in Enzymology (1986), vol. 129 "Precipitation Methods for Quantification of Lipoproteins" pp. 78-100, Academic Press, Inc.

*Primary Examiner*—Michael G. Wityshyn
*Assistant Examiner*—Ralph Gitomer
*Attorney, Agent, or Firm*—Peter J. Dehlinger

[57] ABSTRACT

An improved method for measuring the concentration of HDL-associated cholesterol in a blood-fluid sample. The method includes (a) adding a volume of the sample to an absorptive matrix (i) formed of glass fibers and (ii) effective to separate soluble from precipitated blood through the matrix from a sample-application site to a sample-collection site in the matrix, (b) releasing into the matrix, dextran sulfate and magnesium ions in an amount effective to selectively precipitate LDL and VLDL in the fluid sample, and (c) assaying fluid sample which has migrated through the matrix for the presence of lipoprotein-bound cholesterol. The improvement in the method comprises treating the glass fibers by reaction with bis(hydroxyethyl)aminopropyltriethoxy silane or by coating the fibers with polyvinyl alcohol, thereby affording substantially 100% recovery of HDL applied to the matrix.

1 Claim, 4 Drawing Sheets

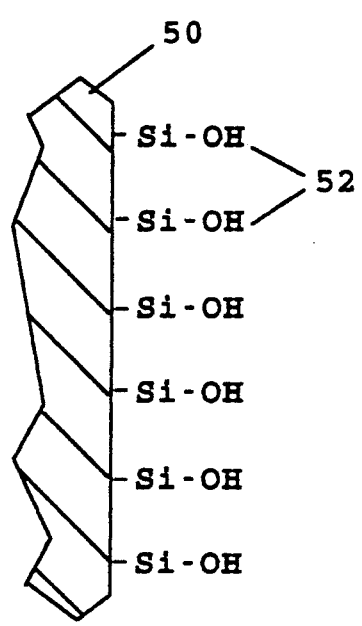
Fig. 5A
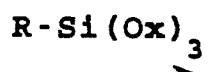 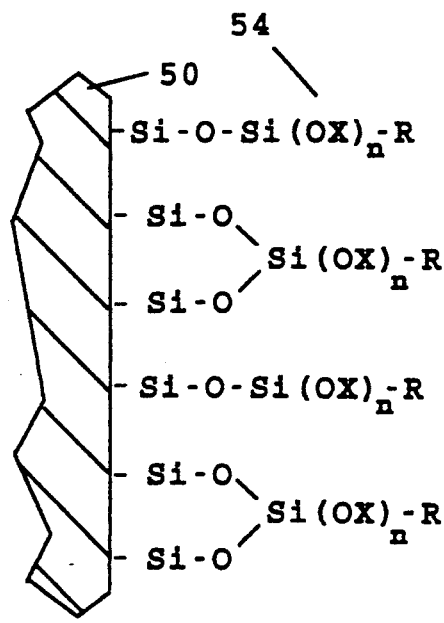
Fig. 5B
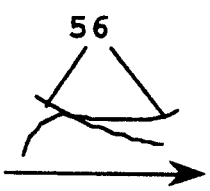 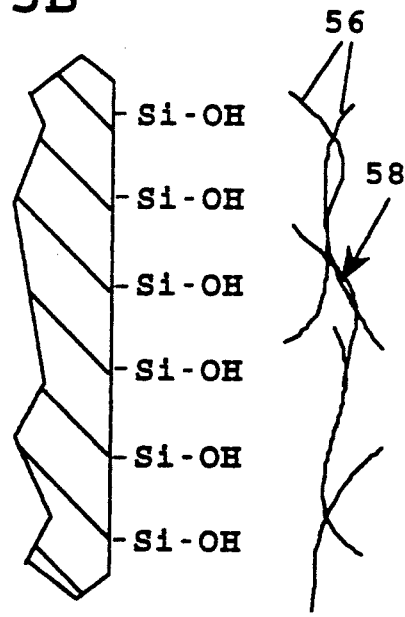
Fig. 5C

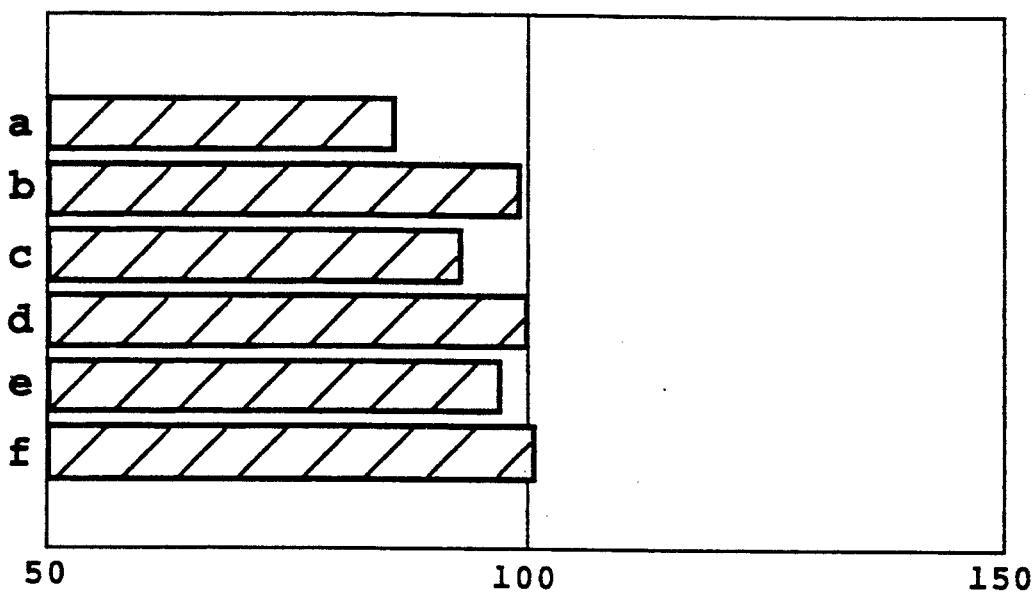
Fig. 6 HDL (% OF CONTROL)
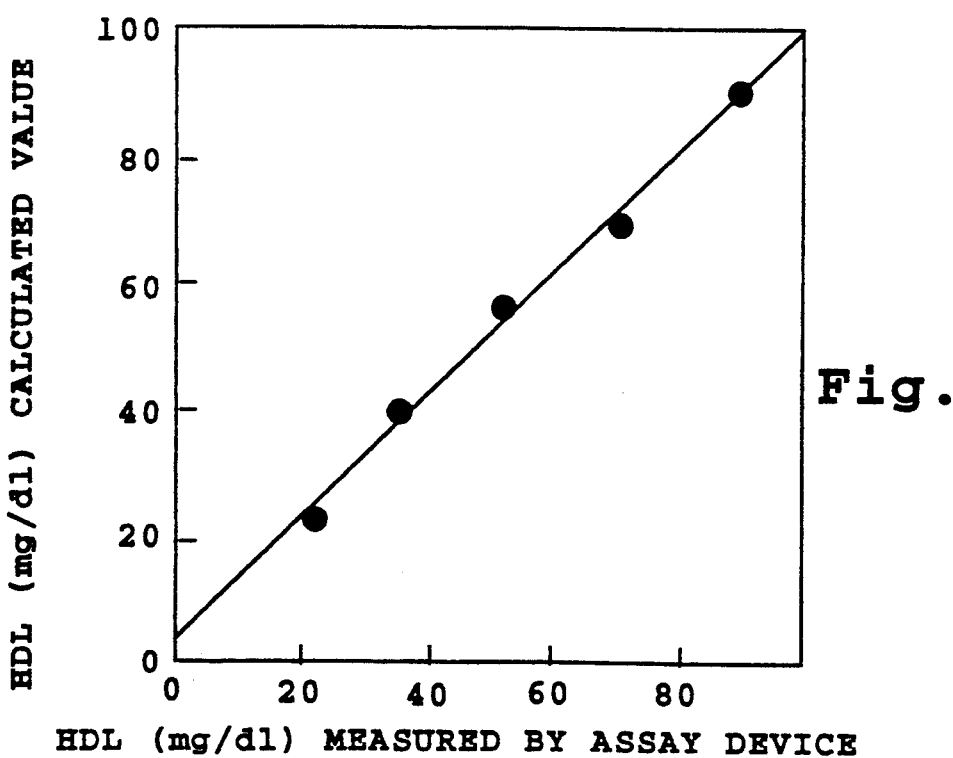
Fig. 7

HIGH-DENSITY LIPOPROTEIN SOLID-BASE PRECIPITATION ASSAY METHOD

This application is a continuation-in-part of U.S. patent application for "Solid-Phase Precipitation Assay Device," Ser. No. 554,147, filed Jul. 16, 1990.

1. FIELD OF THE INVENTION

The present invention relates to a method of determining the concentration of high density lipoprotein (HDL) cholesterol in a blood-fluid sample, and an improved diagnostic assay device for carrying out the method.

2. BACKGROUND OF THE INVENTION

There is a trend toward widespread testing of blood and other body-fluids for analytes which are predictive of health conditions, such as risk of coronary disease. The amount of cholesterol present in the blood is one factor which is related to the risk of coronary artery disease.

Cholesterol circulates in the blood predominantly in the protein-bound form. The proteins which transport cholesterol are the lipoproteins, which are subdivided into three classes based on their density. The very-low density lipoproteins (VLDL) are triglyceride-rich lipoproteins which are synthesized in the liver and ultimately converted to low-density lipoproteins (LDL), which transport most of the plasma cholesterol in humans. The high-density lipoproteins (HDL) are lipoproteins which are involved in the catabolism of triglyceride-rich lipoproteins, and in the removal of cholesterol from peripheral tissues and transport to the liver. An inverse relationship between serum HDL levels and risk of coronary disease has been established. In particular, if the proportion of serum cholesterol associated with HDL is low, the risk of coronary disease is increased.

In view of the importance of relative serum cholesterol levels in risk assessment and management of atherogenic disease, considerable effort has been spent screening large populations of both normal and high-risk individuals for serum levels of HDL, LDL, as well as total cholesterol and triglycerides. The effectiveness of treatments of high-risk individuals has been monitored by regular testing of serum levels of cholesterol in the various lipoprotein compartments.

One method for specific HDL cholesterol testing is based on the selective precipitation of non-HDL lipoproteins in serum by polyanionic compounds, such as dextran sulfate, heparin, and phosphotungstate, in the presence of a group-II cation, such as $Mg^{2+}$, $Mn^{2+}$, and $Ca^{2+}$. The specificity and degree of precipitation are dependent on a variety of factors, including the type and concentration of the polyanion/metal agent. In general, the order of precipitation of serum cholesterol particles, with increasing concentration of polyanion is VLDL, LDL, and HDL. HDL usually remains soluble at concentrations of heparin or dextran sulfate which completely precipitate lower density particles, although minor apoE species of HDL may be coprecipitated with lower density particles. By selective precipitation of lower density particles, HDL serum cholesterol levels can be determined.

In a typical lipid assay procedure, a small volume of blood is drawn and centrifuged to produce a clear plasma or serum sample fluid. The sample fluid is then aliquoted into several assay tubes, for determination of (a) total serum cholesterol, (b) triglycerides, and (c) HDL cholesterol. The HDL sample is precipitated, as above, and the lower density particles are removed by filtration or centrifugation prior to cholesterol detection. The samples are then reacted with an enzyme mix containing cholesterol esterase, cholesterol oxidase, peroxidase and a dye which can be oxidized to a distinctly colored product in the presence of $H_2O_2$. The tubes may be read spectrophotometrically, and the desired total, HDL and LDL cholesterol values determined.

Despite the accuracy and reliability which can be achieved with the liquid-phase cholesterol assay just described, the assay has a number of limitations for use in widespread screening. First, the method uses a venous blood sample, requiring a trained technician to draw and fractionate the blood sample, and aliquot the treated blood to individual assay tubes. At least one of the sample tubes (for HDL determination) must be treated with a precipitating agent, and further processed to remove precipitated material. Although some of these procedures can be automated, analytical machines designed for this purpose are expensive and not widely available outside of large hospitals.

The invention disclosed in above-cited co-pending patent application provides an assay device which substantially overcomes many of the above-mentioned problems associated with liquid-assay procedures for measuring serum cholesterol levels. In one embodiment, the device is designed for measuring the concentration of HDL-associated cholesterol, in a blood sample also containing LDL and VLDL particles. The device includes a sieving matrix capable of separating soluble and precipitated lipoproteins as a fluid sample migrates through the matrix. A reservoir associated with the matrix is designed to release a precipitating agent, for selectively precipitating LDL and VLDL, as fluid sample is drawn into and through the matrix. This allows HDL separation from the precipitated lipoproteins, based on faster HDL migration through the sieving matrix. The fluid sample thus depleted of non-HDL lipoproteins is assayed for cholesterol.

In studies carried out in support of the above invention, it was discovered that exposure of blood fluid samples to the reagent used in precipitating the HDL and LDL particles also resulted in binding of HDL to the glass particles, resulting in spuriously low HDL cholesterol values. This problem is addressed and overcome in the present invention.

3. SUMMARY OF THE INVENTION

A general object of the invention is to provide an improved assay device and method for the determination of HDL in a blood fluid sample.

In one aspect, the invention includes an assay device for measuring serum cholesterol associated with high-density lipoproteins (HDL) in a blood fluid sample also containing low density lipoproteins (LDL) and very low density lipoproteins (VLDL). The device includes a matrix of glass fibers effective to separate soluble from precipitated blood lipoproteins in the fluid sample, as fluid material flows through the matrix from a sample-application site to a sample-collection site in the matrix. The matrix has a preferred fiber density between about 0.16 g/cm$^3$ and 4.0 g/cm$^3$.

A reagent reservoir in the device is designed to release into the matrix, with fluid sample flow through the matrix, a reagent effective to selectively precipitate LDL and VLDL particles. The glass fibers forming the matrix are coated to prevent binding of HDL to the fibers in the presence of the precipitating reagent. Also included in the device is an assay pad to which fluid sample collected at the sample-collection site can be transferred, for HDL cholesterol determination.

In one embodiment, the glass fibers are coated with a hydrophilic polymer, such as polyvinyl alcohol, polyvinyl pyrrolidine, polyethylene glycol, polypropylene glycol, polyethylenimine, polyvinyl sulfonic acid, poly(3-hydroxybutyric acid), polyacrylic acid, poly(3-hydroxyvaleric acid), poly(4-styrene sulfonic acid), poly(2-acrylamido sulfonic acid), or poly-L-glutamate.

In another embodiment, the surface silyl groups of the glass fibers are coated with a silylating reagent having hydrophilic substitutions which forms silyl ether groups, such as silyl mono- and di-ethers of bis(hydroxyethyl)aminopropyltriethoxy silane on the glass surface.

In another aspect, the invention includes a method of measuring serum cholesterol associated with high-density lipoproteins (HDL), employing the assay device just described.

These and other objects and features of the invention will become more fully apparent when the following detailed description of the invention is read in conjunction with the accompanying drawings.

BRIEF DESCRIPTION OF THE DRAWINGS

FIGS. 5A–5C illustrate methods for coating a glass fiber surface (5A) with a silylating agent (5B) or with a hydrophilic polymer (5C);

FIG. 6 is a bar graph showing measured HDL cholesterol values after HDL separation on a glass fiber matrix with the glass fiber coatings indicated in the graph; and FIG. 7 is a plot comparing HDL, cholesterol measured in accordance with the present invention and by a standard liquid-phase approach, where the straight line in the figure indicates ideal conformity between the two tests.

DETAILED DESCRIPTION OF THE INVENTION

A. Assay Device

Figure 1:
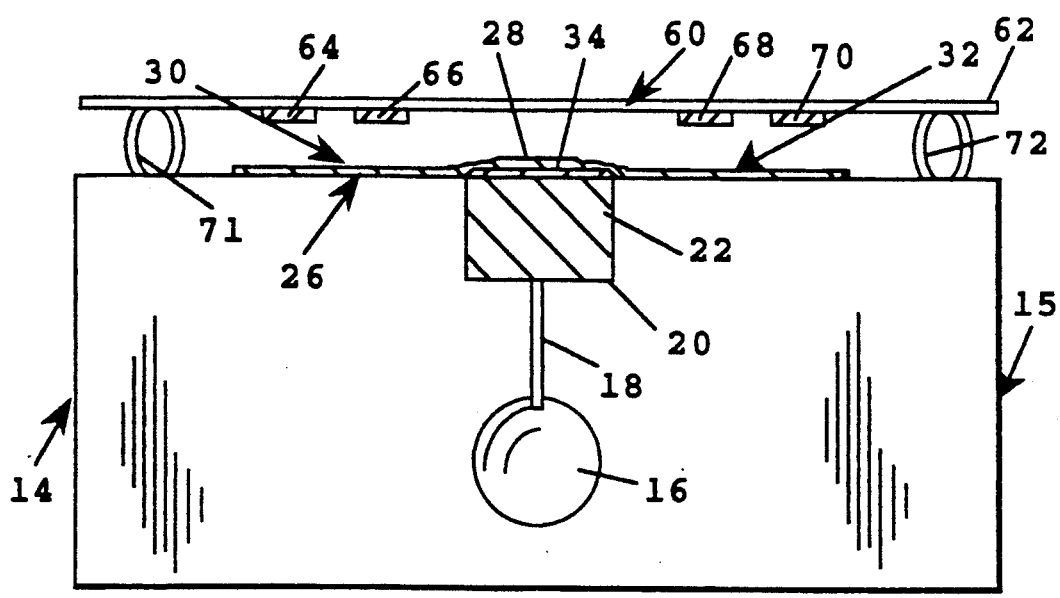
FIG. 1 is a side view of a multi-analyte assay device constructed in accordance with the invention.

FIG. 1 illustrates a multiple-analyte assay device 14 constructed in accordance with the present invention. The device is designed particularly for determining HDL cholesterol using a small volume of blood sample, typically between 10–50 μl of blood. The basic assay configuration of the device has been described in the above-cited U.S. patent application Ser. No. 554,147 for "Solid-Phase Precipitation Assay Device," which is incorporated herein by reference.

The apparatus includes a support 15 which defines a well 16 dimensioned and sized to receive a quantity of a blood sample, typically between about 25–50 μl. A capillary conduit 18 formed in the plate is provided at the base of the well and communicates with notched region 20 formed in the upper edge of the support. The support is preferably a thin plastic plate with the well, tube and notched region formed by standard molding or machining methods.

A sieving pad 22 carried in region 20 functions to partially remove large particulate matter (including blood cells) as the sample migrates through the matrix in a bottom-to-top direction as shown in the figure. Pad 22 is formed of a glass fibrous matrix of material designed to draw aqueous fluid by surface wetting, and to retard the movement of blood cells as the blood sample is drawn through the matrix. That is, the pad serves as a chromatographic medium for separating cell-size particles from soluble serum components on the basis of different migration rates through the medium. One exemplary pad is a glass fiber filter, such as a GF/D or PD008 filter supplied by Whatman, having a packing density of about 0.16 g/cm$^3$. The pad is cut to side dimensions of about 3×8 mm, and a thickness of about 1 mm. The pad is dimensioned to absorb a defined volume of sample fluid, typically about 3–25 μl, and preferably between about 15–25 μl. Sieving pad 22 may additionally contain red blood cell capture reagents such as lectins, antibodies specific for red blood cell surface membrane proteins, thrombin, or ion exchange agents.

Figure 2:
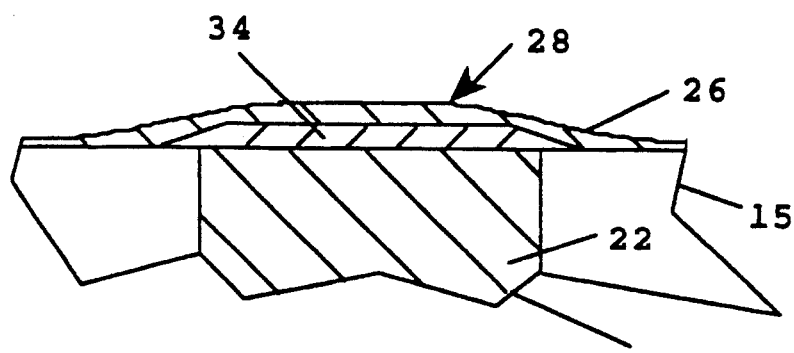
FIG. 2 is an enlarged fragmentary view of the central strip region of the assay device in FIG. 1.

With reference particularly to FIG. 2, the sieving pad, 22, in turn, contacts a reagent reservoir, 34, described below, which may be separate from or integral to an elongate strip or matrix 26 which is attached to and extends along an interior portion of the plate's upper edge. Matrix 26 serves to distribute sample fluid from a central sample-application region 28 of the strip, which is adjacent reservoir 34 in contact with pad 22, to opposite sample-collection regions 30, 32 adjacent the ends of the matrix (FIG. 1). The matrix is preferably formed of coated glass fibers, as will be described below.

The packing density and thickness of the matrix are such as to absorb and distribute small fluid volumes, e.g., 10–25 μl, supplied to the sample-application region of the strip to the sample-collection regions of the strip. The matrix has a preferred packing density between about 0.16 g/cm$^3$ and 4.0 g/cm$^3$. One exemplary strip material is BSB-20 glass fiber filter available from Whatman having a packing density of about 0.2 gm/cm$^3$, a width of about 3 mm, a length of about 3 cm, and a thickness of about 0.12 mm.

Figure 3:
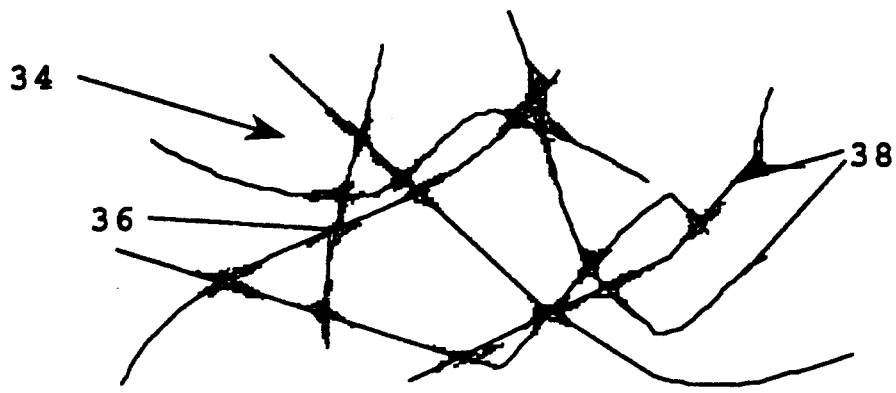
FIG. 3 is an enlarged view of one type of slow-release reservoir employed in the device.

With continued reference to FIG. 2, a reagent reservoir 34 in the device contains a precipitating agent used to selectively precipitate LDL and VLDL particles in the fluid sample, as fluid sample is drawn into the sample-application region of the matrix. FIG. 3 shows an enlarged portion of reagent reservoir. In this embodiment, the precipitating agent is formulated in a binder and dried to form regions of dried reagent 36 on the glass fibers, such as fibers 38.

The reservoir is designed to release the precipitating agent at a rate which maintains the concentration of agent in the sample fluid entering the matrix, and more specifically, at least the first 10% and preferably 20–40% of the total sample fluid which is drawn into the matrix between the sample-application and sample-collection sites on the matrix, within a concentration range which is effective to selectively precipitate or aggregate the non-HDL compounds in the sample fluid.

The preferred precipitating agent is a sulfonated polysaccharide, such as dextran sulfate (which has a typical molecular weight of 50,000 daltons) in combination with magnesium acetate or chloride, buffered to maintain neutral pH.

The binder material and proportion of binder to precipitating agent in the formulation are selected to provide gradual particle dissolution over the period when sample fluid is drawn into the matrix, and more specifically, when the first 10–40% or more of total sample fluid is drawn into the matrix. Preferred polymer binders, and methods of applying the binder and reagent to the fibers in the matrix, have been detailed in above-cited U.S. patent application for "Solid-Phase Precipitation Assay Device", Ser. No. 554,147, filed Jul. 16, 1990, which is incorporated herein by reference.

Figure 4:
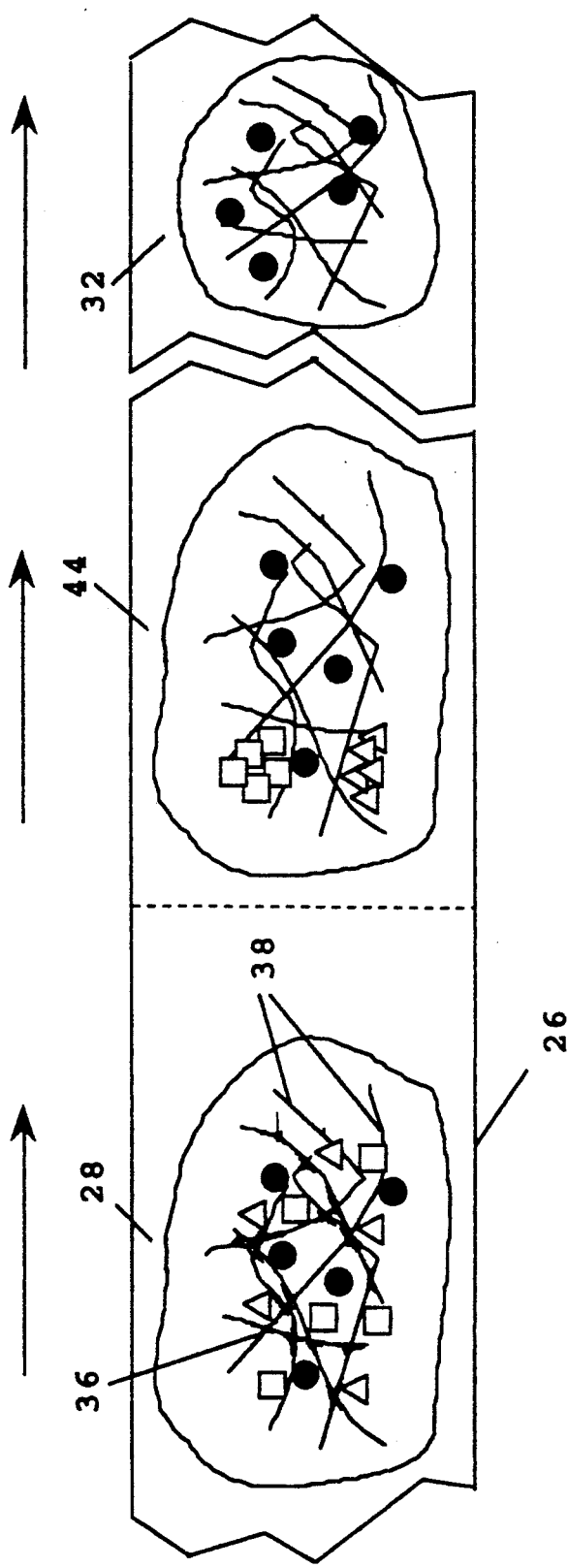
FIG. 4 illustrates release of precipitating agent and precipitation of LDL (open squares) and VLDL (open triangles) in a serum sample (left side of the figure) and the separation of HDL (solid circles) particles from precipitated LDL and VLDL which form after migration through the strip in the device in the direction indicated by the arrows.

FIG. 4 illustrates the operations of selective precipitation and separation which occur between sample-application and sample-collection regions in matrix 26, during an assay for determination of HDL in a serum sample. The different lipoproteins in the sample are indicated by solid circles (HDL), open squares (VLDL), open triangles (LDL), and clusters of the units (aggregates). The fluid sample flows through the matrix from left to right, as indicated by the arrows.

The left portion of FIG. 4 shows the sample-application region 28 of the matrix, with the cutaway portion showing the fibers 38 of the matrix and regions 36 of reagent contained on the fibers. The fluid sample in this region contains all of the original lipoprotein components at original lipoprotein concentrations, as indicated.

The central portion of the figure shows a portion 44 of matrix 26, downstream from the reagent reservoir, between the sample-application site 28 and a sample-collection site 32. As the sample fluid is drawn through the web in the reservoir, the deposit on the web is slowly dissolved, releasing precipitating agent into the sample. As the cholesterol-containing particles in the solvent front are drawn toward the sample-collection region to the right in the figure, the aggregated and non-aggregated particles are separated chromatographically. As indicated in the center cutaway portion, LDL and VLDL lipoproteins are largely in precipitated, or aggregated, form.

The right portion of the figure shows a portion of the matrix at the sample-collection site 32. Here the composition of fluid sample which first reaches the sample-collection region is substantially free of non-HDL particles, but contains HDL particles at concentrations present in the originally applied blood sample.

According to an aspect of the invention, it has been discovered that treatment of blood with reagents used in selectively precipitating non-HDL blood lipoproteins results in binding of a proportion of the HDL present in the sample to non-coated glass fibers, i.e., glass fibers of the type supplied in commercially available glass filters. The reduction in measured HDL cholesterol resulting from this binding to the glass fibers will be seen below with respect to FIG. 6.

According to an important feature of the invention, the glass fibers in the separation matrix are prepared to contain a coating which is effective to prevent binding of HDL to the glass fibers in the presence of a precipitating agent, such as a sulfonated polysaccharide. Two preferred types of coating and their method of preparation are illustrated in FIGS. 5A–5C. FIG. 5A shows a fragmentary surface portion of a glass fiber 50 having silyl hydroxyl (Si—OH) surface groups, such as groups 52. The silyl hydroxyl groups are typical of glass fiber surfaces in commercial glass filters and the like. Although not shown here, the fiber may also be formulated to contain a small percentage (less than about 2% by weight) of a polymer, such as polyvinyl alcohol (PVA) which is formulated with the glass, prior to formation, to improve the packing properties of the glass fibers.

In the coating method shown in FIG. 5B, the glass filter is coated by chemically reacting the surface silyl hydroxyl groups with a hydrophilic silylating agent having the general form $R—Si(OX)_n$, where R is a hydrophilic group, X is a lower alkyl, preferably methyl or ethyl radical, and n is 2 or 3. Exemplary silylating agents include silyl mono and di-ethers of bis(hydroxyethyl)aminopropyltriethoxy silane.

The reaction is carried according to known methods for silylating glass. In a typical procedure, a 2% aqueous "working" solution of the silylating reagent, such as bis(hydroxyethyl)aminopropyl triethoxysilane is prepared from a 62% stock solution obtained commercially, e.g., Huls America (Petrarch Systems, Bristol, Pa.). The glass filter forming the matrix is dipped into freshly prepared working solution for at least 10 minutes, rinsed with 95% ethanol, and dried in an oven at 50° C. for 5 minutes.

As seen in FIG. 5B, the silylating reagent can react with either one or two Si—OH surface groups, forming a silyl mono- or di-ethers coating, indicated at 54. This coating masks the surface Si—OH groups of untreated glass, replacing these groups with hydrophilic R groups of the type indicated above.

In a second general embodiment, illustrated in FIG. 5C, the glass filter is coated with a hydrophilic polymer, such as indicated at 56. In a preferred method for applying the polymer coating, the glass filter forming the matrix is dipped in a solution of polyvinyl alcohol (PVA), followed by drying at elevated temperature (about 90° C.) for several minutes. Final incorporation of polymer, as estimated by comparison of mass before and after flame vaporization of the organic compound from the glass filter, is approximately 5% of dry weight. FIG. 5C shows the resulting polymer coating 58 formed of polymer fibers. As with the chemical modification method, the coating is effective to mask surface Si—OH groups and replace them with the hydrophilic groups of the polymer subunits.

Preferred polymers for use in the invention include polyvinyl alcohol, polyvinyl pyrrolidine, polyethylene glycol, polypropylene glycol, polyethylenimine, polyvinyl sulfonic acid, poly(3-hydroxybutyric acid), polyacrylic acid, poly(3-hydroxyvaleric acid), poly(4-styrene sulfonic acid), poly(2-acrylamido sulfonic acid, or poly-L-glutamate. Preferred polymer molecular weights are between about 10–200 kilodaltons. Preferred polymer content is greater than about 4% polymer, measured as described above, with reference to polyvinyl alcohol as standard.

The effect of various glass compositions and surface coatings on binding of HDL to glass filter fibers can be seen from the study shown in FIG. 6. In this study, each of six glass filters, treated as described below, was used as the sieving matrix. In each case, a serum sample previously treated with dextran sulfate-Mg precipitating reagent to remove LDL and VLDL was passed through the filter, then analyzed for HDL-associated cholesterol content by a conventional cholesterol assay.

As a control, the same sample was analyzed directly by the solution-phase method, without passage through the filter. HDL cholesterol concentration for the filtered material was then expressed as percent of unfiltered material.

As shown in the top bar (a) in the graph in FIG. 6, passage of a serum sample through untreated glass fiber (Whatman BSB-20) resulted in about a 15% loss of HDL cholesterol content, due to binding of HDL to the glass of the matrix. According to manufacturer's specifications, the glass fibers on this filter are formulated with about 1% PVA incorporated into the glass filter during formation, to improve matting properties of the fibers.

The same filter material, after silylation with bis(hydroxyethyl)aminopropyl triethoxysilane, showed almost no binding of HDL, as evidenced by HDL cholesterol content equivalent to that of the control sample (b). The same filter material, when coated with a solution of PVA, at less than 4% polymer by weight (c), exhibited less binding than untreated fibers. Filters having a 4-5% PVA coating by weight (d) showed no appreciable HDL binding. From these results it can be determined that for the fiber composition used in this study, a 4-5% PVA coating was sufficient to prevent binding of HDL to the filter material. Additional studies suggested that the precise amount of PVA coating required is dependent upon the composition and particularly the glass fiber density of the filter material employed.

Also shown in FIG. 6 is the result of filtration of sample through glass filters formed by the manufacturer to include 6% PVA by weight. These filters were not specifically surface coated with PVA, according to the methodology described above. Passage of sample through this filter resulted in a slight decrease in HDL-cholesterol content of the filtrate (e). The decreased HDL binding to this filter suggests that the added PVA serves in part to coat and mask Si—OH groups ordinarily on the glass fiber surface. When 6% PVA-augmented fiber material was additionally silylated, using the silylation methodology described above, no appreciable loss of HDL-cholesterol content of sample due to binding of HDL to the filter was observed (f).

The study indicates that both chemical coating by hydrophilic silylation groups and polymer coating by a hydrophilic polymer (at a sufficient polymer concentration) are effective to prevent binding of HDL to glass fibers in the presence of precipitating agent.

Completing the description of FIG. 1, device 14 includes a test plate 60 composed of an elongate support 62, and multiple wettable, absorbent reaction test pads 64, 66, 68 and 70, carried on the lower surface of the support, at the positions shown. The support is transparent or has transparent windows which allow the pads to be viewed through the support. The reaction test pads in the test plate are attached to the support by a transparent or translucent adhesive material, or by sonic welding or other suitable bonding method. Each pad used in a particular assay contains analyte-dependent reagents effective to produce an analyte-dependent change in the pad which can be detected optically, either visually or by a detector, in a known manner. All or any integral subset of the pads may be employed in a particular assay. The nature of the reagents for the cholesterol assay is described below.

Desirably, the reaction pads are porous, fused polymer or microporous polymer membranes having a thickness, after complete penetration of the fluid, of about 100-150$\mu$ and side dimensions of about 3 mm. The absorption volume of each pad is preferably between about 0.5-2 $\mu$l. A preferred composition material of the reaction pads is polysulfone.

When the serum reaches the sample-collection sites, such as site 32 adjacent the ends of matrix 26, test plate 60 is moved until test pads 64, 66, 68, 70 are in contact with the matrix. In this position, sample fluid in the matrix is drawn into the adjacent pad by capillary flow with fluid movement occurring in a direction normal to the pad surfaces. The plate is held at this position until a desired degree of wetting of the pads is achieved.

The test plate is mounted on support 15 by a pair of resilient members, such as elastomeric blocks 71, 72. The blocks act to bias the pads toward a non-transfer position at which the pads are spaced apart from the dispenser's sample-transfer surface, with a spacing typically of between about 0.5 to 1.0 mm.

The cholesterol-dependent reagents in the test pad produce a change in the pad which can be detected optically, either visually or by a detector, in a known manner. One preferred apparatus for reading the signal levels of the pads, and for calculating a corrected analyte value based on the readings is described in co-owned U.S. patent application for Controlled-Volume Assay Method and Apparatus, Ser. No. 320,474, filed Mar. 8, 1989, which is incorporated herein by reference. Each of the test pads contains reagent components for converting $H_2O_2$ to a colored signal reaction product. The components include peroxidase, and a coupled dye system which is converted by the peroxidase, in the presence of $H_2O_2$, to a distinctively colored signal reaction product. Enzymatic color reactions which employ a variety of substrate-specific oxidases, for enzymatic generation of $H_2O_2$, and subsequent oxidation of a dye to form a colored reaction product are well known. The HDL pads also contain cholesterol esterase for releasing free cholesterol from HDL, and cholesterol oxidase, for producing $H_2O_2$ by reaction with free cholesterol in the sample fluid.

The two reference standard pads contain, in addition to the common-pathway components, different known amounts of a non-cholesterol reference compound, preferably a D-amino acid, and an oxidase, such as D-amino acid oxidase, for generating $H_2O_2$ when the pad is wet with sample fluid.

The reaction components present in reaction and reference pads are summarized in Table 1.

TABLE I

| Components | Reference | Reaction |
|---|---|---|
| HDL Sample (HDL) | + | + |
| cholesterol esterase | | + |
| cholesterol oxidase | | + |
| D-amino acid | + | |
| D-amino acid oxidase | + | |
| peroxidase + dye(s) | + | + |

In the above assay device, the amount of reference compound added to each reference standard is selected to produce, in the presence of a given volume of defined reaction mixture, a signal level corresponding to a known concentration of cholesterol, assayed under identical conditions in the presence of cholesterol oxidase. The actual reference standard produced in the assay will also depend on (a) the amount of soluble interfering compounds present in the serum sample (as distinguished from non-HDL compounds which interfere with the measurement of HDL cholesterol), (b) the condition of the reaction components in the pad, and (c) reaction conditions, including temperature and reaction time.

The signal values measured for the duplicate HDL pads are plotted on the standard curve, and the known correspondence between reference standard and cholesterol concentrations is used to determine the cholesterol concentration in each of these pads. It will be appreciated that the cholesterol values so calculated are (a) calculated on the basis of a standard curve, and (b) self-corrected for variations in reaction conditions, and for inhibitory effects and loss of activity of common-pathway components, assuming that all four reaction pads are subject to the same variations in these factors. The concentration of cholesterol associated with HDL can be calculated from the average in cholesterol concentration determined from the two HDL sample pads.

EXAMPLE 1

Assay for HDL

An assay device like that described in FIG. 1 was prepared using the preferred filter materials described in Section A. Stock solution A contained 2 g/100 ml 50,000 dalton dextran sulfate. Stock solution B contained 1M magnesium acetate. To a ⅜" by 5/16" by 150 micron thick glass fiber filter was added 0.75 ∥ l each of stock solutions A and B and 2.21 ∥ l water. The pad was dried for 20 minutes at 50° C. and assembled into the reservoir region (34) of the device, as described above.

Four test pads in the device contained the reagents described above for reference standard and cholesterol determination. Each reaction pad was prepared from a 150 micron thick polysulfone filter (TR 450; Gelman Sciences, Ann Arbor, Mich.) cut into 2×4 mm rectangles. The two reaction test pads for cholesterol determination were infused with 10 µl of a reagent solution containing 150 U/ml cholesterol ester hydrolase, 10 U/ml cholesterol oxidase, 80 U/ml peroxidase, and 20 mM 4-aminoantipyrine (4-AAP) and 80 mM N-ethyl-N-sulfohydroxypropyl-M-toluidine (TOOS), in reduced form, in Tris-HCl or phosphate buffer at neutral pH. The two test pads for the reference standards contained a layer infused with 40 U/ml D-amino acid oxidase, 80 U/ml peroxidase, and 20 mM 4-aminoantipyrine (4-AAP) and 80 mM TOOS, in reduced form, in the Tris-HCl or phosphate buffer, then dried. Next, 3 µl of 20 mM D-amino acid in ethanol were added, and the pad was dried. The amounts of reference standard were calibrated, in a liquid-phase assay containing a defined reaction buffer, and under defined reaction conditions, and matched with similarly measured cholesterol concentrations from a predetermined volume of known-concentration solution of cholesterol in non-ionic detergent. After drying under reduced pressure, the reaction test pads were assembled and attached to the test plate support in the device.

A whole blood sample from a human test subject was obtained conventionally, and applied to the well in the device in an amount sufficient to wet the four reaction test pads. The wetted test pads were incubated at room temperature for 90 seconds, or until no further color development was observed.

The analyte-related signal was read by reflectance spectrophotometry, at an illuminating wavelength of 500 nm. The values for the reference standard pads were plotted to give a two-point self-corrected standard curve from which the cholesterol readings were calculated.

EXAMPLE 2

Serum HDL Assay

The assay device used was similar to that described with reference to FIG. 1, and was prepared using the reservoir, as described in Example 1, containing a dextran sulfate (MW 50,000)-Mg precipitating reagent at neutral pH. The reaction pad formulations were as described in Example 1, for enzymatic determination of cholesterol. The a ⅜" by 5/16" by 150 micron thick glass fiber filter was coated with 5% polyvinyl alcohol by weight, and otherwise used as in Example 1, above.

Five samples were prepared from human serum to contain known amounts of HDL cholesterol, with concentrations varied over the range from 15–100 mg/dL, with evenly spaced dilutions. The HDL cholesterol of all samples were measured in triplicate in the assay device, with results as shown in Table 2:

TABLE 2

| SAMPLE# | MEASURED HDL mg/dL | CALCULATED HDL mg/dL |
|---|---|---|
| 1 | 22.8 | 22.8 |
| 2 | 37.5 | 40.3 |
| 3 | 54.3 | 57.7 |
| 4 | 75.4 | 75.1 |
| 5 | 92.5 | 92.5 |

The calculated or theoretical values (y-axis) were plotted against the results obtained for the samples when measured in the assay device of the invention, as shown in FIG. 7.

As shown by this example, the improved assay device of the present invention provides HDL measurements which have the same accuracy as liquid-phase tests, which, in contrast to the present invention, require venous blood samples and involved liquid sample handling.

Although the invention has been described with reference to particular embodiments and configurations, it will be appreciated by one skilled in the art that various changes and modifications may be made without departing from the invention.

I claim:

1. In a method of measuring serum cholesterol associated with high-density lipoproteins (HDL) in a blood fluid sample also containing low density lipoproteins (LDL) and very low density lipoproteins (VLDL), comprising (a) adding a volume of the sample to an absorptive matrix (i) formed of glass fibers, and (ii) effective to separate soluble from precipitated blood lipoproteins in such fluid sample, as fluid sample flows through the matrix from a sample-application site to a sample-collection site in the matrix, (b) releasing into the matrix, dextran sulfate and magnesium ions in an amount effective to selectively precipitate LDL and VLDL in the fluid sample, and (c) assaying fluid sample which has migrated through the matrix for the presence of lipoprotein-bound cholesterol, an improvement for increasing the percent of sample HDL which migrates through the matrix and is assayed, comprising treating the glass fibers by reaction with bis(hydroxyethyl)aminopropyltriethoxy silane or by coating the fibers with 4–5% by weight polyvinyl alcohol, thereby affording substantially 100% recovery of HDL applied to the matrix.

* * * * *